United States Patent
Webster et al.

(10) Patent No.: US 12,296,184 B2
(45) Date of Patent: May 13, 2025

(54) PROVIDING WEARABLE DEVICE INFORMATION TO RESCUERS

(71) Applicant: WEST AFFUM HOLDINGS DAC, Dublin (IE)

(72) Inventors: Brian D. Webster, Mercer Island, WA (US); Phillip D. Foshee, Jr., Woodinville, WA (US); David P. Finch, Bothell, WA (US); Steven E. Sjoquist, Lynnwood, WA (US)

(73) Assignee: West Affum Holdings DAC, Dublin (IE)

( * ) Notice: Subject to any disclaimer, the term of this patent is extended or adjusted under 35 U.S.C. 154(b) by 512 days.

(21) Appl. No.: 17/581,444

(22) Filed: Jan. 21, 2022

(65) Prior Publication Data

US 2023/0086186 A1 Mar. 23, 2023

Related U.S. Application Data

(60) Provisional application No. 63/247,250, filed on Sep. 22, 2021.

(51) Int. Cl.
*A61N 1/39* (2006.01)
*A61N 1/04* (2006.01)
(Continued)

(52) U.S. Cl.
CPC ......... *A61N 1/3904* (2017.08); *A61N 1/0484* (2013.01); *A61N 1/3993* (2013.01); *G16H 40/67* (2018.01); *G16H 80/00* (2018.01)

(58) Field of Classification Search
None
See application file for complete search history.

(56) References Cited

U.S. PATENT DOCUMENTS 3,724,355 A 4/1973 Busch et al.
3,724,455 A 4/1973 Unger
(Continued)

FOREIGN PATENT DOCUMENTS

DE 102005060985 A1 6/2007
EP 2305110 A1 4/2011
(Continued)

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.
(Continued)

*Primary Examiner* — Carl H Layno
*Assistant Examiner* — Manolis Pahakis
(74) *Attorney, Agent, or Firm* — Polsinelli PC

(57) ABSTRACT

Technologies and implementations for a wearable healthcare system including an information management module (IMM). The IMM may be configured to detect proximity of a healthcare device. The IMM may be configured to determine a type of the detected healthcare device. Once the type of healthcare device is determined, the IMM may be configured to communicate information regarding a medical device, where the communicated information may be adapted to correspond to the determined type of healthcare device.

19 Claims, 6 Drawing Sheets

US 12,296,184 B2

Page 2

(51) Int. Cl.
*G16H 40/67* (2018.01)
*G16H 80/00* (2018.01)

(56) References Cited

U.S. PATENT DOCUMENTS

| | | | |
|---|---|---|---|
| 4,583,524 A | 4/1986 | Hutchins |
| 4,619,265 A | 10/1986 | Morgan et al. |
| 4,666,432 A | 5/1987 | McNeish et al. |
| 4,698,848 A | 10/1987 | Buckley |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,348,008 A | 9/1994 | Bornn et al. |
| 5,353,793 A | 10/1994 | Bornn |
| RE34,800 E | 11/1994 | Hutchins |
| 5,394,892 A | 3/1995 | Kenny |
| 5,405,362 A | 4/1995 | Kramer et al. |
| 5,429,593 A | 7/1995 | Matory |
| 5,474,574 A | 12/1995 | Payne et al. |
| 5,618,208 A | 4/1997 | Crouse et al. |
| 5,662,690 A | 9/1997 | Cole et al. |
| 5,708,978 A | 1/1998 | Johnsrud |
| 5,741,306 A | 4/1998 | Glegyak et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,280,461 B1 | 8/2001 | Glegyak et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder |
| 6,427,083 B1 | 7/2002 | Owen et al. |
| 6,437,083 B1 | 7/2002 | Owen et al. |
| 6,450,942 B1 | 9/2002 | Lapanashvili et al. |
| 6,529,875 B1 | 3/2003 | Nakajima |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,099,715 B2 | 8/2006 | Korzinov et al. |
| 7,212,850 B2 | 5/2007 | Prystowsky et al. |
| 7,559,902 B2 | 7/2009 | Ting et al. |
| 7,587,237 B2 | 9/2009 | Korzinov et al. |
| 7,753,759 B2 | 7/2010 | Pintor et al. |
| 7,865,238 B2 | 1/2011 | Brink |
| 7,870,761 B2 | 1/2011 | Valentine et al. |
| 7,907,996 B2 | 3/2011 | Prystowsky et al. |
| 7,941,207 B2 | 5/2011 | Korzinov |
| 7,974,689 B2 | 7/2011 | Volpe et al. |
| 8,135,462 B2 | 3/2012 | Owen et al. |
| 8,140,154 B2 | 3/2012 | Donnelly et al. |
| 8,369,944 B2 | 2/2013 | Macho et al. |
| 8,527,028 B2 | 9/2013 | Kurzweil et al. |
| 8,548,557 B2 | 10/2013 | Garstka et al. |
| 8,560,044 B2 | 10/2013 | Kurzweil et al. |
| 8,615,295 B2 | 12/2013 | Savage et al. |
| 8,644,925 B2 | 2/2014 | Volpe et al. |
| 8,676,313 B2 | 3/2014 | Volpe et al. |
| 8,706,255 B2 | 4/2014 | Phillips et al. |
| 8,742,349 B2 | 6/2014 | Urbon et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,084,583 B2 | 7/2015 | Mazar et al. |
| 9,089,685 B2 | 7/2015 | Sullivan et al. |
| 9,119,547 B2 | 9/2015 | Cazares et al. |
| 9,131,901 B2 | 9/2015 | Volpe et al. |
| 9,132,267 B2 | 9/2015 | Kaib |
| 9,265,432 B2 | 2/2016 | Warren et al. |
| 9,345,898 B2 | 5/2016 | Piha et al. |
| 9,408,548 B2 | 8/2016 | Volpe et al. |
| 9,445,719 B2 | 9/2016 | Libbus et al. |
| 9,454,219 B2 | 9/2016 | Volpe et al. |
| 9,579,020 B2 | 2/2017 | Libbus et al. |
| 9,592,403 B2 | 3/2017 | Sullivan |
| 9,598,799 B2 | 3/2017 | Shoshani et al. |
| 9,675,804 B2 | 6/2017 | Whiting et al. |
| 9,724,008 B2 | 8/2017 | Sullivan et al. |
| 9,878,171 B2 | 1/2018 | Kaib |
| 9,895,105 B2 | 2/2018 | Romem |
| 9,901,741 B2 | 2/2018 | Chapman et al. |
| RE46,926 E | 7/2018 | Bly et al. |
| 10,016,613 B2 | 7/2018 | Kavounas |
| 10,076,656 B2 | 9/2018 | Dar et al. |
| 10,192,387 B2 | 1/2019 | Brinig et al. |
| 10,307,133 B2 | 6/2019 | Kaib |
| 10,463,867 B2 | 11/2019 | Kaib et al. |
| 10,589,110 B2 | 3/2020 | Oskin et al. |
| 10,599,814 B2 | 3/2020 | Landrum et al. |
| 2002/0013538 A1* | 1/2002 | Teller .................. A61B 5/0002 |
| | | 128/903 |
| 2002/0181680 A1 | 12/2002 | Linder et al. |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2005/0204310 A1* | 9/2005 | De Zwart ............. G16H 40/63 |
| | | 715/713 |
| 2006/0173499 A1 | 8/2006 | Hampton et al. |
| 2008/0312709 A1 | 12/2008 | Volpe et al. |
| 2009/0005827 A1 | 1/2009 | Weintraub et al. |
| 2010/0007413 A1 | 1/2010 | Herleikson |
| 2010/0298899 A1 | 11/2010 | Donnelly et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0191476 A1 | 7/2012 | Reid et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0144355 A1 | 6/2013 | Macho et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0012144 A1 | 1/2014 | Crone |
| 2014/0025131 A1 | 1/2014 | Sullivan et al. |
| 2014/0046391 A1 | 2/2014 | Cowan et al. |
| 2014/0070957 A1 | 3/2014 | Longinotti-Buitoni et al. |
| 2014/0163663 A1 | 6/2014 | Poddar et al. |
| 2014/0324112 A1 | 10/2014 | Macho et al. |
| 2014/0378812 A1 | 12/2014 | Saroka et al. |
| 2015/0002606 A1* | 1/2015 | Hyde .................... H04N 7/14 |
| | | 348/14.02 |
| 2015/0039053 A1 | 2/2015 | Kaib et al. |
| 2015/0161554 A1 | 6/2015 | Sweeney et al. |
| 2015/0297135 A1 | 10/2015 | Shoshani et al. |
| 2015/0328472 A1 | 11/2015 | Sullivan et al. |
| 2016/0004831 A1 | 1/2016 | Carlson et al. |
| 2016/0076175 A1 | 3/2016 | Rock et al. |
| 2016/0076176 A1 | 3/2016 | Rock et al. |
| 2016/0082277 A1 | 3/2016 | Foshee, Jr. et al. |
| 2016/0113581 A1 | 4/2016 | Amir et al. |
| 2016/0256104 A1 | 9/2016 | Romem et al. |
| 2016/0283900 A1 | 9/2016 | Johnson et al. |

(56) References Cited

U.S. PATENT DOCUMENTS

| | | |
|---|---|---|
| 2017/0014073 A1 | 1/2017 | Shoshani et al. |
| 2017/0027469 A1 | 2/2017 | Amir et al. |
| 2017/0036066 A1 | 2/2017 | Chahine |
| 2017/0040758 A1 | 2/2017 | Amir et al. |
| 2017/0049386 A1* | 2/2017 | Abraham ............ A61M 5/1723 |
| 2017/0162840 A1 | 6/2017 | Pendry |
| 2017/0258401 A1* | 9/2017 | Volpe .................... H04W 4/023 |
| 2017/0319862 A1 | 11/2017 | Foshee, Jr. et al. |
| 2017/0367591 A1 | 12/2017 | Jorgensen |
| 2018/0116537 A1 | 5/2018 | Sullivan et al. |
| 2018/0117299 A1 | 5/2018 | Gustavson et al. |
| 2018/0184933 A1 | 7/2018 | Sullivan et al. |
| 2018/0185662 A1 | 7/2018 | Foshee, Jr. et al. |
| 2018/0243578 A1 | 8/2018 | Volosin |
| 2018/0361165 A1 | 12/2018 | Jaax et al. |
| 2019/0030352 A1 | 1/2019 | Sullivan et al. |
| 2019/0076666 A1 | 3/2019 | Medema |
| 2019/0082968 A1* | 3/2019 | Karnik ..................... A61B 5/01 |
| 2019/0116896 A1 | 4/2019 | Armour et al. |
| 2019/0321650 A1 | 10/2019 | Raymond et al. |
| 2020/0275249 A1* | 8/2020 | Kim ................... H04W 12/0431 |
| 2022/0070666 A1* | 3/2022 | Hua ...................... H04L 9/3271 |

FOREIGN PATENT DOCUMENTS

| | | |
|---|---|---|
| EP | 3380189 B1 | 10/2018 |
| JP | 4320257 B2 | 8/2009 |
| JP | 2014526282 A | 10/2014 |
| JP | 5963767 B2 | 8/2016 |
| WO | 1998039061 A2 | 9/1998 |
| WO | 2011/146448 A1 | 11/2011 |
| WO | 2012064604 A1 | 5/2012 |
| WO | 2012/151160 A1 | 11/2012 |
| WO | 2015/056262 A1 | 4/2015 |

OTHER PUBLICATIONS

Lifecor LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Heartstart MRx and XL AED Algorithm—Application Note, Jul. 2001, Edition 2 Philips Healthcare, USA.

The LifeVest Network/Patient Data Management System, Zoll, 2015, 20C0503 Rev A.

Metting Van Rijn, A. C., Peper A., & Grimbergen, C. A., High-Quality Recording of Bioelectric Events Part 1: Interference Reduction, Theory and Practice, Review, Medical & Biological Engineering & Computing, Sep. 1990, pp. 389-397, IFMBE.

Pagan-Carlo, et al., "Encircling Overlapping Multipulse Shock Waveforms for Transthoracic Defibrillation," JACC Journals, Dec. 1998, vol. 32 Issue 7, p. 2065-2071.

Zoll, LifeVest, Proven protection from Sudden Cardiac Death, 2017, Pittsburgh PA, USA, 4 pages.

International Search Report and Written Opinion for PCT Application No. PCT/US2015/051726, dated May 20, 2016, European Patent Office, Rijswijk, 11 pages.

* cited by examiner

400 A computer program product

402 A signal bearing medium 404 at least one of
machine readable non-transitory medium having stored therein instructions that, when executed by one or more processors, operatively enable an information management module (IMM) to:

receive an indication of proximity of a healthcare device from a proximity sensor, the indication including healthcare device identification information and distance information of the healthcare device from a wearable medical device (WMD);

determine a type of healthcare device based upon the received healthcare device identification information; and communicate information regarding the WMD, the communicated information adapted to correspond to the determined type of healthcare device.

| 406 a computer-readable medium | 408 a recordable medium | 410 a communications medium |

Figure 4

PROVIDING WEARABLE DEVICE INFORMATION TO RESCUERS

RELATED APPLICATION

This application claims benefit of priority to U.S. Provisional Patent Application Ser. No. 63/247,250, filed on Sep. 22, 2021, titled PROVIDING WEARABLE DEVICE INFORMATION TO RESCUERS, which is incorporated herein by reference in its entirety for all purposes.

INFORMATION

Unless otherwise indicated herein, the approaches described in this section are not prior art to the claims in this application and are not admitted to be prior art by inclusion in this section.

Technology has contributed to improvements in healthcare. Some examples include healthcare related devices that may be capable of determining various health related information about a person. For example, a healthcare device may be capable of determining health related information of an electrical activity of a person. The electrical activities of the person may include various electrical activities of various organs such as, but not limited to, brain activities, heart activities, skin moisture, gastrointestinal tract activities, breathing activities, etc.

The healthcare device may be included as part of a wearable system, where the wearable system may include a healthcare device configured to be worn by a person (WMD) facilitating a more continuous monitoring and/or treatment of various health related issues of the person. For example, the WMD may be configured to monitor the electrical activities and/or treat potential health related issues of the heart. An example of a WMD for monitoring the electrical activities of the heart may be wearable cardioverter defibrillator (WCD).

The wearable system having the WMD may receive and store variety of information about the health of the person and any treatment that may have been administered to the person by the WMD. The variety of information may be informative to various people that may come in contact with the person wearing the WMD (e.g., a medical personnel, a layperson, an emergency personnel). Additionally, the WMD may provide guidance/instructions to facilitate treatment of the person. The information and/or guidance/instructions may not be of use to everyone, who may be considered a first responder to the person wearing the WMD. For example, information, that may be related to clinical information (e.g., electrocardiogram/ECG, electric charge that may have been administered, time of the heart related event, etc.) may not be of use to a layperson. However, the clinical information may be of use to a medical professional and/or an emergency personnel. Similarly, the guidance/instructions provided by the WMD may not be applicable to various first responders. For example, guidance/instructions that may include inquiries as to various status of the person wearing the WMD (e.g., "please confirm the person is breathing", "please call 911", etc.), that may be considered to be directed towards a layperson first responder, may not be of use to a medical professional and/or an emergency personnel.

All subject matter discussed in this section of this document is not necessarily prior art and may not be presumed to be prior art simply because it is presented in this section. Plus, any reference to any prior art in this description is not and should not be taken as an acknowledgement or any form of suggestion that such prior art forms parts of the common general knowledge in any art in any country. Along these lines, any recognition of problems in the prior art are discussed in this section or associated with such subject matter should not be treated as prior art, unless expressly stated to be prior art. Rather, the discussion of any subject matter in this section should be treated as part of the approach taken towards the particular problem by the inventor(s). This approach in and of itself may also be inventive. Accordingly, the foregoing summary is illustrative only and not intended to be in any way limiting. In addition to the illustrative aspects, embodiments, and features described above, further aspects, embodiments, and features will become apparent by reference to the drawings and the following detailed description.

SUMMARY

Described herein are various illustrative wearable device systems and methods for managing communication of information regarding a wearable medical device (WMD). Example systems may include the WMD, a proximity sensor, and an information management module (IMM). The IMM may be communicatively coupled to the proximity sensor and be configured to receive an indication of proximity of a healthcare device, where the indication may include a medical identification information and distance information of the healthcare device from the WMD. Additionally, the IMM may be configured to determine a type of healthcare device based, at least in part, on the received medical identification information. The IMM may be configured to communicate information regarding the WMD, where the communicated information may be adapted to correspond to the determined type of healthcare device.

The foregoing summary is illustrative only and not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

FIG. 4 illustrates an example computer program product, arranged in accordance with at least some embodiments described herein.

DETAILED DESCRIPTION

Figure 1:
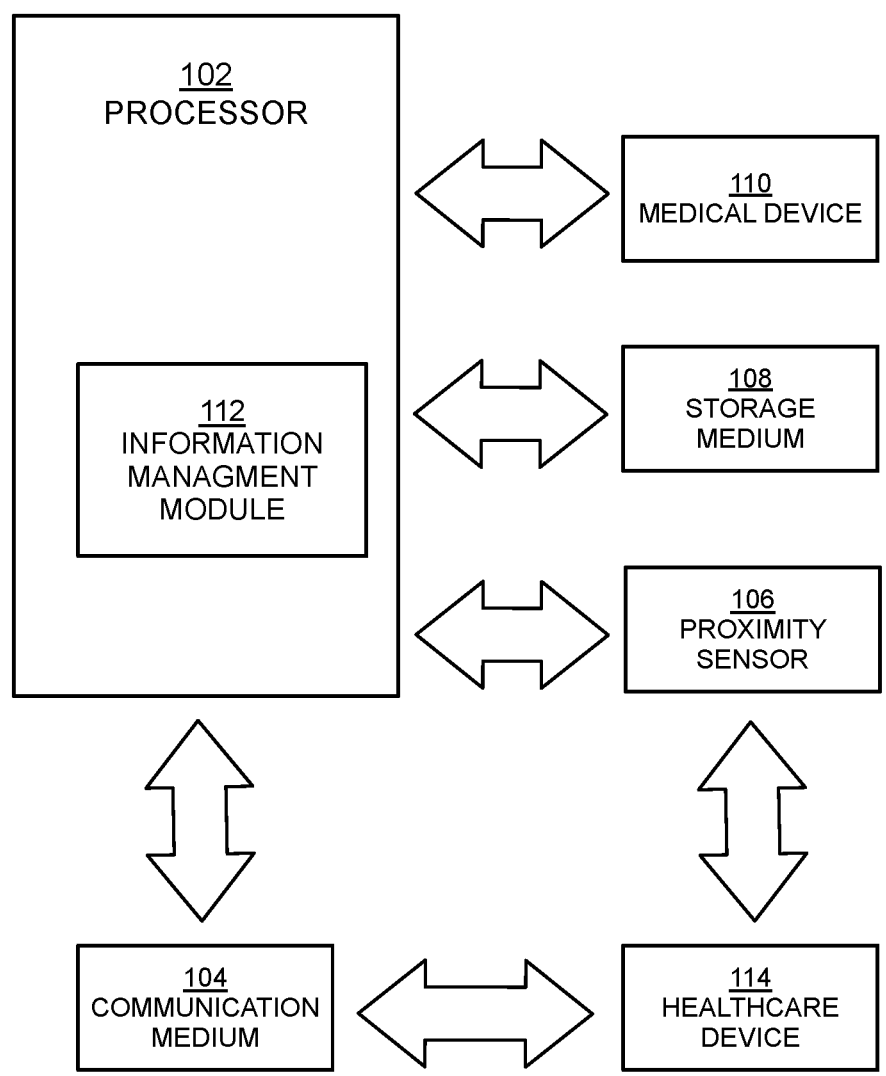
FIG. 1 illustrates a block diagram of a system for managing communication of information regarding a medical device in accordance with various embodiments.

The following description sets forth various examples along with specific details to provide a thorough understanding of claimed subject matter. It will be understood by those skilled in the art after review and understanding of the present disclosure, however, that claimed subject matter may be practiced without some or more of the specific details disclosed herein. Further, in some circumstances, well-known methods, procedures, systems, components and/or circuits have not been described in detail in order to avoid unnecessarily obscuring claimed subject matter.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

This disclosure is drawn, inter alia, to methods, apparatus, and wearable device systems related to managing communication of information regarding a wearable medical device (WMD). The managing the communication may include adapting the communicated information to correspond to a type of healthcare device detected by the wearable device system. Additionally, as an extension of the adapting, the communicated information may be of use to a person, who may be associated with the type of healthcare device (e.g., emergency and/or medical professional).

For the purposes of providing a detailed description of the claimed subject matter, utilization of a WMD may be described as included in a wearable system of the present disclosure. However, in various embodiments, the wearable system of the present disclosure may include a variety of wearable devices such as, but not limited to, cardiac event monitors, Holter monitors, mobile cardiac telemetry (MCT) devices, brain activity monitors, wearable cardioverter defibrillators (WCDs), mobile devices (e.g., a mobile/smart phones), etc. Accordingly, the claimed subject matter is not limited in this respect.

Utilizing the example of a wearable system including a WMD, the WMD may be configured to facilitate monitoring of electrical signals such as, but not limited to, monitoring of electrical signals from a heart of a person. For example, the WMD may be configured to monitor and treat potential issues with the heart (i.e., the person may have a health condition, where the electrical control system of the heart may malfunction causing the heart to beat irregularly or not at all). In some examples, these types of WMDs may include a defibrillator device. An example of a WMD, which may be configured to monitor and treat potential issues with the heart, may include a wearable cardioverter defibrillator (WCD). In the present disclosure, for the purposes of ease of understanding the various embodiments of the claimed subject matter, references may be made to a medical device such as, but not limited to, a WCD, where information regarding the WCD may be managed and communicated as disclosed in the various embodiments herein.

As part of the description of a WMD related to the activities of the heart, some issues with the heart may be briefly described. For example, some issues with the rate of the heartbeat may be generally referred to as an arrhythmia. Arrhythmia may be caused by many factors, but in general, an arrhythmia may be caused by a malfunction in the electrical control system of the heart. Some types of arrhythmias may result in inadequate blood flow resulting in reduction or lack of the amount of blood pumped to the various parts of the body. For example, issues with the sinoatrial (SA) node may lead to arrhythmia of some kind. Some arrhythmias may lead to a condition known as sudden cardiac arrest (SCA). In an SCA condition, the heart may fail to pump blood effectively, and as a result, death may occur.

An example type of an arrhythmia, which may be associated with SCA, may be a condition known as ventricular fibrillation (VF). VF may be a condition where a ventricle or ventricles, which make up the heart to facilitate the pumping of blood, may make uncoordinated movements instead of steady rhythmic movements. In the VF condition, the heart may not pump adequate amounts of blood or may not pump blood at all, which may eventually lead to death. Another type of arrhythmia, which may be associated with SCA, may be a condition known as ventricular tachycardia (VT).

Turning back to the WMD configured to be utilized to monitor and/or provide therapy to the heart, the medical device may be capable of monitoring the electrical signals of the heart and if necessary, administer therapy to the heart in the form of an electric shock. The WMD may monitor the electrical signals and provide the electric shock to the heart externally (i.e., through the surface of a body) via components commonly known as electrodes, where some of the electrodes may be monitoring electrodes and some of the electrodes may be therapy electrodes. The medical device may be in the form of a cardioverter defibrillator. The medical device may be included in a support structure configured to be worn by the person. In this example, the medical device may help facilitate monitoring the electrical activities of the heart and provide the electric shock to the heart in the VF condition. As a result, the medical device may help prevent Sudden Cardiac Death (SCD).

Before turning the figures, some non-limiting example scenarios of utilization of various embodiments of wearable device systems may be described. In the non-limiting example scenarios, a person may have a heart condition, where the person may utilize a medical device, which could be wearable by the person such as, but not limited to, a wearable medical device (WMD). As mentioned, the WMD may be configured to facilitate monitoring and treatment of a heart condition of the person such as, but not limited to, a wearable cardioverter defibrillator (WCD). The WCD may include a support structure configured to be worn by the person such as, but not limited to, a garment (e.g., a vest). Included in the support structure of the WCD, a WCD monitor may include various components to facilitate the functionality of the WCD. A number of electrodes, monitoring electrodes and therapy electrodes, may be communicatively coupled with the WCD monitor. Accordingly, in the non-limiting example scenarios, the wearable device systems may include a WCD. Additionally, the wearable device systems may include a proximity sensor and an information management module (IMM).

In one example scenario, a wearable device system may include a WCD, a proximity sensor, and an information management module, where the IMM may be communicatively coupled to the proximity sensor. The IMM may be configured to receive an indication of proximity of a healthcare device apart from the WCD. The indication may include healthcare device identification information and distance information of the healthcare device from the WCD. The IMM may be configured to communicate information regarding the WCD, where the communicated information may be adapted to correspond to the determined type of healthcare device.

Continuing with this example scenario, the WCD may be worn by a person. As the person wears the wearable device system, the WCD may receive various electrical signals such as, but not limited to, electrocardiogram (ECG) signals, and the ECG signals may be stored by the WCD. At some point, the person may experience a heart related event (e.g., an arrhythmia of some kind). The received ECG signals may indicate the onset of the heart related event, and in response, the WCD may provide a therapy signal (e.g., electric shock) to treat the heart. In this example scenario, a layperson may have witnessed the person suffering the heart related event. The layperson may obtain a publicly available automated external defibrillator (AED) and go over to the person. The IMM may receive an indication that an AED is nearby via the proximity sensor. The indication may include healthcare identification information about the AED such as, but not limited to, information that the AED may be the publicly available kind (i.e., may not be an AED commonly used by emergency and/or medical personnel, but instead, an AED that may be used by a layperson). Additionally, the IMM may determine how far the AED may be located from the person (i.e., WCD). Because the IMM may have determined that the AED is the kind commonly used by a layperson, the IMM may communicate information regarding the WCD adapted to correspond to the type of AED. In this scenario, the IMM may communicate information via audio by generating an audio message such as, but not limited to, "do not remove the WCD", "do not shock patient with your AED", "dial 911", and so forth. The audio message may include some audio instructions that may be applicable to the layperson such as, but not limited to, "is the person breathing", "please start chest compressions", "is the person unconscious", etc. The audio instructions may be conveyed via a speaker included in the wearable device system. As a result, the communicated information may be adapted to the type of healthcare device (i.e., layperson healthcare device).

In one example, the AED in the above scenario may include an electronic tag such as, but not limited to, a tag configured to utilize a variety of wireless protocols such as, but not limited to, Wi-Fi, Bluetooth, Near-Field Communication, Radio-frequency identification (RFID), various IEEE 802 based wireless communication including Zigbee, cellular wireless communication, etc. The tag may include healthcare device identification information, which may be communicated to the IMM as described.

In another example scenario, an emergency personnel such as, but not limited to, an emergency medical technician (EMT), may have approached the person suffering the heart event. The IMM may determine that a healthcare device in proximity may be a professional healthcare device (e.g., a professional AED that may be commonly used by an EMT). In this scenario, the IMM may communicate information regarding the WCD that may be of use by the EMT. For example, the IMM may communicate information regarding the WCD such as, but not limited to, a time when the heart related event was detected (e.g., the time an arrhythmia was detected by the WCD), elapsed time since the heart related event was detected, a number of shocks delivered to the heart by the WCD responsive to the heart related event, energy level of the shocks delivered, and so forth (i.e., information related to the monitoring and/or therapy of the person by the WCD). This information may be communicated via audio device (e.g., speaker included in the WCD). In addition to or alternatively, the IMM may communicate information regarding the WCD to the professional healthcare device (i.e., the professional AED used by the EMT). In this example, the professional AED may have a display, which may be utilized as a user interface (e.g., audio replay, information displayed as text, graphical display of information, etc.), to display the information communicated from the WCD. Further, the information may be stored to be subsequently provided to a medical personnel (e.g., a nurse, a medical doctor, etc.). As a result, the communicated information may be adapted to the type of healthcare device and the be of use to the person, who may be associated with the healthcare device.

In one example, the EMT in the above scenario may have an EMT associated device or a tag, which the EMT may have on their person. For example, a name tag, an identifying patch on an article of clothing, radio, mobile phone, tablet, wrist band, necklace, watch, etc. The tag on the EMT may include some form of near field communication solution such as, but not limited to, RFID. In this example, when the EMT approaches the person suffering the heart event, the IMM may detect the device that may be associated with the EMT (e.g., name tag). The IMM may communicate adapted information to the healthcare device associated with the EMT that may be of use to the EMT. The information adapted to be communicated by the IMM regarding the WCD to be utilized by the EMT may facilitate a hand off of the treatment of the person to the EMT. The communicated information may include a replay functionality such as, but not limited to, a verbal rewind and replay.

In another example, the information adapted to be communicated by the IMM regarding the WCD to be utilized by the EMT to facilitate a handoff of the treatment of the person to the EMT may be transferred utilizing a computer aided dispatch (CAD) system. The CAD system may be a combination of hardware and software that may track information such as, but not limited to, when a 911 call was made, the nature of the call (e.g., nature of the emergency, length of time of the call, etc.), phone number, location information, information that may be of use to the responding emergency personnel, information that may be of use to a medical personnel, and so forth. Some examples of communication utilizing a CAD system may be found in commonly-owned U.S. Patent Application Publication No. US2018/0221645, titled: WEARABLE CARDIAC DEFIBRILLATOR SYSTEMS & METHODS & SOFTWARE FOR CONTACTING NON-WITNESSING RESPONDERS, which is incorporated herein by reference for all purposes.

In another example, an EMT may have a smart phone that may be detected by the IMM. In this example, the IMM may communicate information to an application, which may be included in the smart phone of the EMT. The application may facilitate access of information that may be of use to the EMT from the WCD. Additionally, the application may be configured to facilitate real-time communication between the EMT and a medical personnel (e.g., a portal with a medical doctor). The application may be configured to receive information from the IMM regarding the WCD, and the information in turn may be communicated to the medical personnel. The information from the WCD may include clinical information that may be of use to the medical personnel. The information communicated by the IMM to the medical personnel may be audio and/or visual.

In some other examples, the IMM may be configured to establish a wireless COMLINK with a device and/or tag or smartphone of an emergency personnel to communicate information regarding the WCD, where the information may be adapted to be of use to the emergency personnel. In this example, instead of a direct hand off of the treatment of the person to the EMT via communication of information device-to-device, a device and/or tag, or smartphone of a third party may be configured to verbally and/or visually communicate information to a bystanders or an emergency personnel. Accordingly, appropriate information about the status of the person wearing the WCD may be communicated to the bystander or to the emergency personnel at the scene of the person even without the utilization of the COMLINK between two medical devices. Some examples of COMLINK may be found in commonly-owned U.S. Patent Application Publication No. US2014/0043149, titled: MOBILE COMMUNICATION DEVICE & APP FOR WEARABLE DEFIBRILLATOR SYSTEM, which is incorporated herein by reference for all purposes.

In some other examples, the IMM may be configured to establish a wireless COMLINK with a device and/or tag or smartphone of an emergency personnel to communicate information regarding the WCD, where the device and/or tag or smartphone may include a Kestra EMT Application available from Kestra Medical Technologies, Inc. of Kirkland, Washington. In this example, the IMM may be configured to utilize the device and/or tag or smartphone as a hub to facilitate establishment of the wireless COMLINK with a professional healthcare device and/or the device and/or tag or smartphone of the emergency personnel.

In some other examples, a mobile device associated with the WCD (i.e., mobile device associated with the person wearing the WCD), may include an EMT communication method (e.g., a button). If the EMT button is activated, the IMM may be configured to communicate information regarding the WCD locally (e.g., locally at the WCD or remotely to another device and/or location). The communication may be visual (e.g., display on the mobile device) and/or audio (e.g., via speaker on the mobile device). The communicated information may be adapted to be of use for the emergency personnel (e.g., professional/clinical information) regarding the person.

In some other examples, the person wearing the medical device may have been shocked (i.e., therapy has been administered by the WCD), and the IMM may have detected the proximity of a professional medical device (e.g., professional defibrillator, which may be utilized by EMT or some medical personnel). Additionally, the IMM may have determined that the EMT associated device and/or tag, or a smartphone may have the Kestra EMT App. In this example, the IMM may be configured communicate information regarding the WCD adapted to be of use by the emergency/medical personnel via the Kestra EMT App.

In another example, the IMM may be configured to facilitate a down time for an emergency/medical personnel. In this example, after a therapy shock may have been administered by the WCD worn by the person, an alert communication method may have been activated (e.g., a button). In response, the IMM may be configured to detect and determine the type of healthcare device as previously described and communicate adapted information regarding the WCD (e.g., elapsed time since a shockable event was detected). The alert communication method may be the EMT communication method as described, which may be configured to be operable after therapy shock may have been administered by the medical device worn by the person. Here again, the IMM may be configured to detect and determine the type of healthcare device as previously described and to indicate elapsed time since a shockable event was detected (e.g., an arrythmia detection). In both of these example scenarios, the heart rate may not have been converted after the therapy shock was administered to the person wearing the medical device.

In one example, the IMM may be configured to facilitate access of information of the medical device of the person an emergency personnel (e.g., information that may be of use to the emergency personnel may be displayed on the medical device and/or a mobile device associated with the person).

In another example, the IMM may be configured to communicate information, which may include a downloadable application, to a device associated with the type of device detected by the IMM. For example, the IMM may have detected a device associated with a layperson in proximity of the person wearing the medical device. The layperson may have a mobile device (e.g., smartphone). The IMM may be configured to communicate to the layperson that the medical device of the person includes a downloadable application for assistance of the person (e.g., visually via a decal or on a display, audio via speaker, etc.). The downloadable application may facilitate gathering and communication of information of use to an emergency and/or a medical personnel. If the layperson is acceptable to downloading the application, the layperson may utilize their smart phone to directly contact the medical device, where the IMM may be configured to facilitate the download (e.g., wireless communication such as, but not limited to near field communication/NFC, Bluetooth, Infrared/IR, Wi-Fi, etc.). Alternatively, the IMM may be configured to display a machine readable code (e.g., quick response/QR code), which may facilitate installation of the application on the smart phone of the layperson.

In some examples, the IMM may be configured to communicate information gathered by the medical device of the person in parallel or serially over a time period. For example, the IMM may be configured to communicate information (i.e., upload) to a remote centralized location via a mobile device with a one or more mobile applications. In this example, various information of the person may be communicated to a central location to facilitate evaluation and/or modifications of the medical device. The information communicated may include clinical information of use to a medical personnel, which may facilitate review and approval of functionality of the medical device and/or the health condition of the person.

In some examples, the IMM may be configured to facilitate communication of remainder of information related to the medical device of the person to the centralized location responsive to the person, a caregiver, emergency personnel, or a healthcare personnel requesting the initiation of the communication of the information. In some other examples, the person, the caregiver, emergency personnel, or the healthcare personnel may utilize an application on a mobile device to initiate communication of information from the medical device to the remote centralized location as managed by the IMM.

In some other examples, an IMM included in several medical devices may be coordinated to communicate information regarding their respective medical devices to a remote location. For example, the person wearing the medical device suffers a heart event (e.g., an arrythmia). The medical device may have provided a therapy shock, but the shock failed to convert (i.e., correct the heart rate). While waiting for emergency personnel to arrive, a layperson may approach the person with an AED (e.g., layperson AED commonly found in public spaces). As described, the IMM of the medical device may communicate information to the layperson and/or the AED. Again, the AED utilized may also fail to convert. When the emergency personnel (e.g., EMT) arrives with their professional medical device (i.e., professional defibrillator), the IMM may communication information regarding the medical device to the EMT and/or the professional defibrillator as described. The two or more of the three devices, medical device of the person, the AED, and the professional defibrillator, may each include an IMM. The IMMs included in each of the devices involved may coordinate communication of information regarding their respective devices to a mobile device of the person. The mobile device of the person may optionally communicate the coordinated information from the IMMs to a remote location.

Turning now to FIG. 1, FIG. 1 illustrates a block diagram of a system for managing communication of information regarding a medical device in accordance with various embodiments. In FIG. 1, a system 100 may include a processor 102, a communication medium 104, a proximity sensor 106, storage medium 108, and medical device 110. The communication medium 104, the proximity sensor 106, the storage medium 108, and the medical device 110 may be all be communicatively coupled with the processor 102. Additionally, the processor 102 may include an information management module (hereon, IMM 112). The medical device 110 may be a medical device such as, but not limited to, a wearable medical device (WMD). The storage medium 108 may include information regarding the medical device, such as, but not limited to, physiological information of a person utilizing the medical device 110 (e.g., ECG), activity information related to the medical device 110 (e.g., shock level and time of shock), and so forth.

In FIG. 1, the proximity sensor 106 may be configured to detect proximity of a healthcare device 114. Upon detection by the proximity sensor 106 of the healthcare device 114, the IMM 112 may receive an indication of proximity of the healthcare device from the proximity sensor 106, where the indication may include healthcare device identification information and distance information of the healthcare device from the medical device 110. The IMM 112 may determine a type of healthcare device 114 based upon the received healthcare device identification information. In FIG. 1, once the IMM 112 determines the type of healthcare device 114, the IMM 112 may communicate, via the communication medium 104, information regarding the medical device 110, where the communicated information may be adapted to correspond to the determined type of healthcare device as described in the various embodiments disclosed herein.

Figure 5:
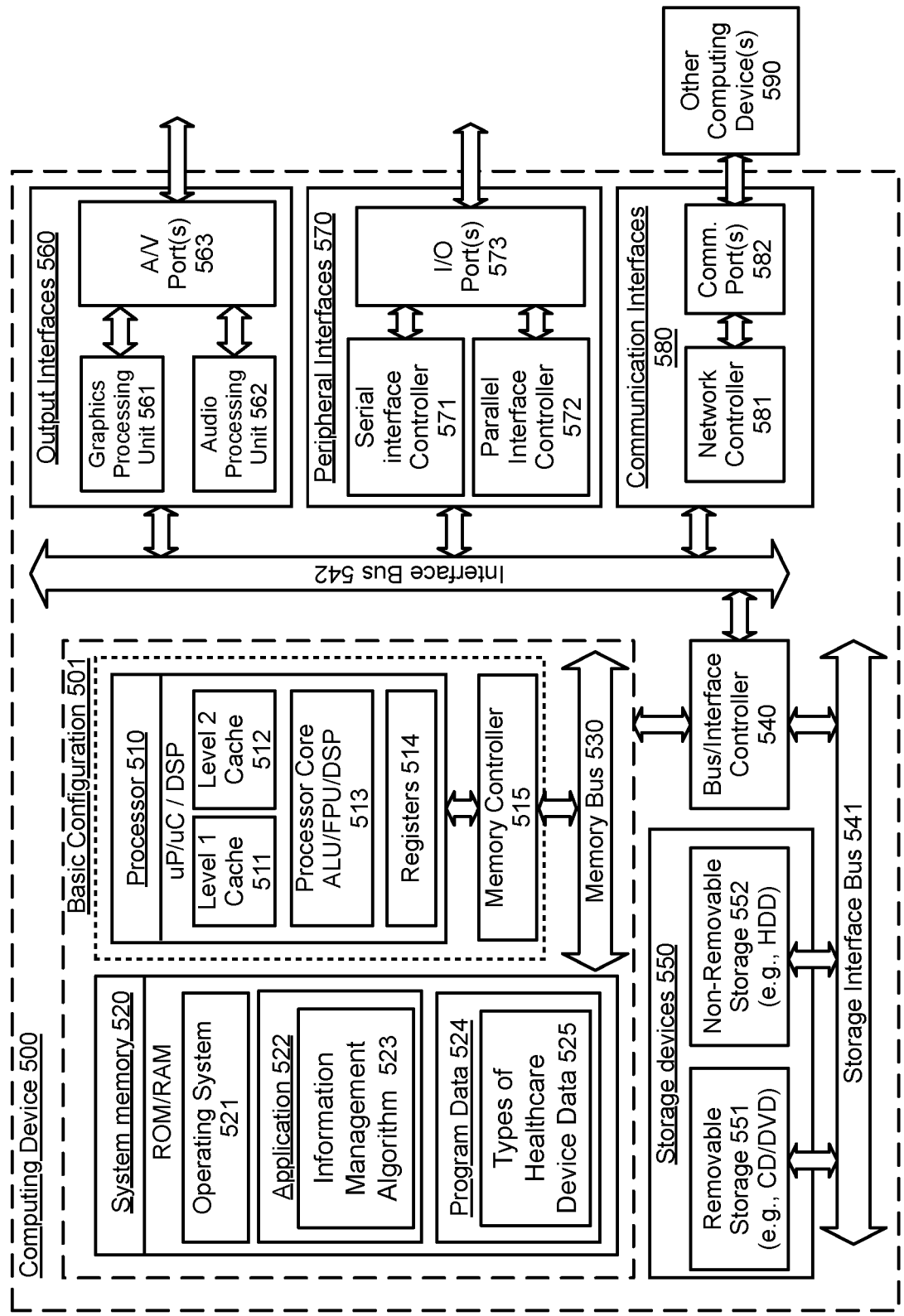
FIG. 5 is a block diagram illustrating an example computing device, such as might be embodied by a person skilled in the art, which is arranged in accordance with at least some embodiments of the present disclosure.
Figure 6:
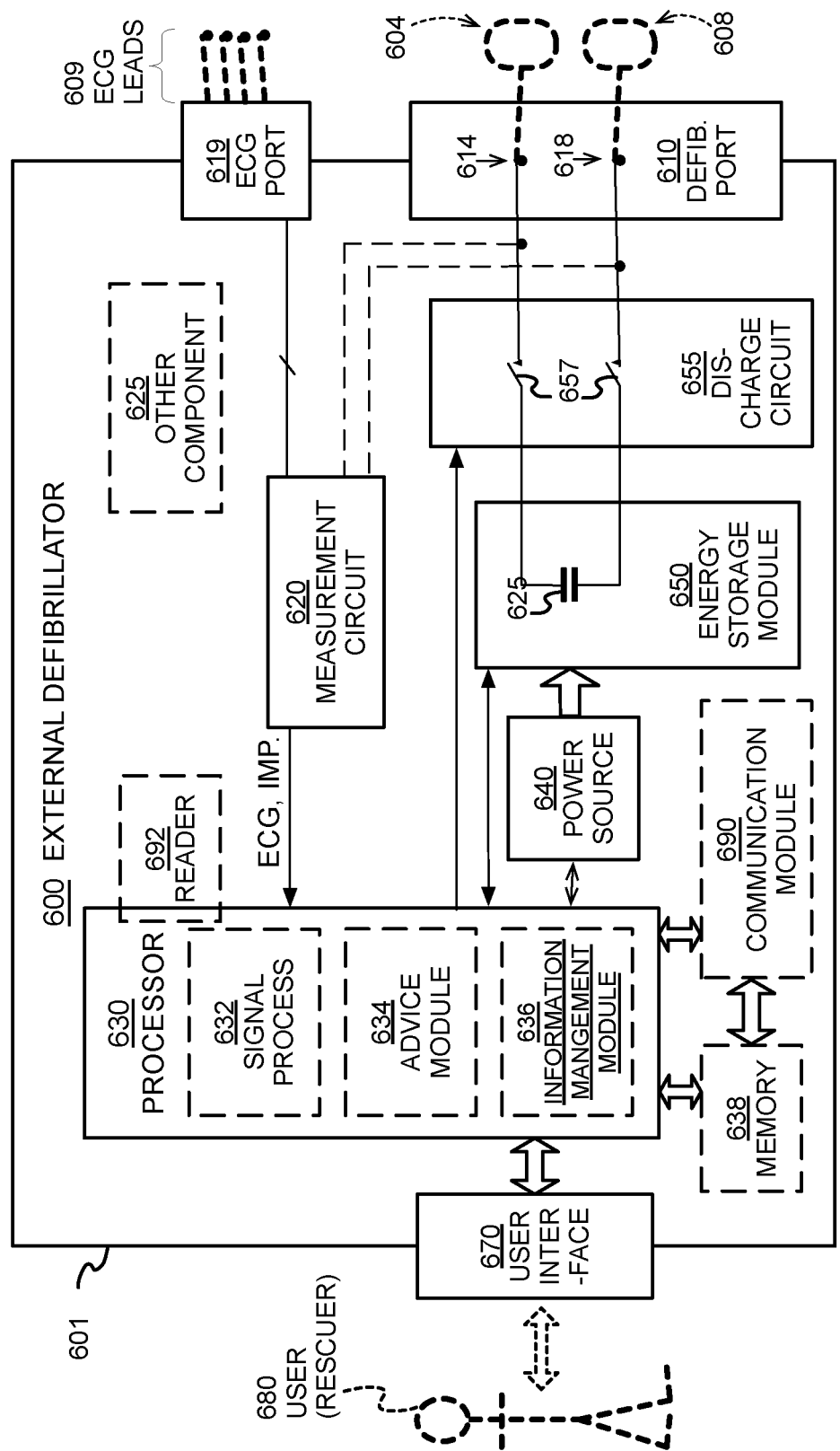
FIG. 6 is a block diagram illustrating components of a medical device, which may be used with various embodiments.

In various embodiments, the system 100 may be included in a wide variety of medical devices and healthcare devices such as, but not limited to, wearable medical devices (WMDs), wearable cardioverter defibrillator (WCDs), electronic tags, Some further details of the system 100 may be found with respect FIGS. 5 and 6.

In FIG. 1, the processor 102 may be a wide variety of processors to facilitate at least some of the functionality described herein such as, but not limited to, machine learning capable processors. Some of examples of machine learning capable processors may include processors available from Intel Corporation of Santa Clara, Calif. (e.g., Nervana™ type processors), available from Nvidia Corporation of Santa Clara, California (e.g., Volta™ type processors), available from Apple Company of Cupertino, California (e.g., A11 Bionic™ type processors), available from Huawei Technologies Company of Shenzen, Guangdong, China (e.g., Kirin™ type processors), available from Advanced Micro Devices, Inc. of Sunnyvale, California (e.g., Radeon Instinct™ type processors), available from Samsung of Seoul, South Korea (e.g., Exynos™ type processors), and so forth. Accordingly, the claimed subject matter is not limited in this respect.

Figure 2:
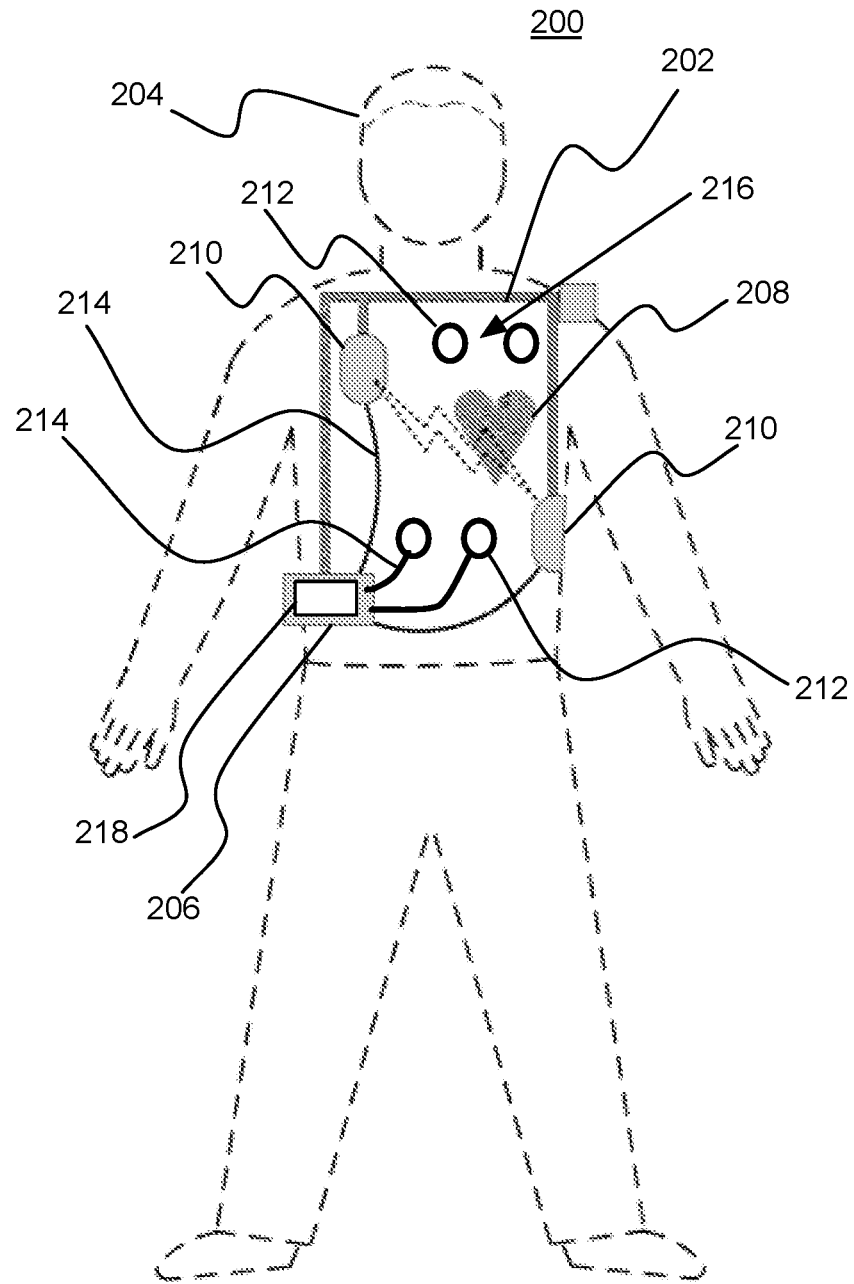
FIG. 2 illustrates an example of a medical device that may be utilized, in accordance with at least one or more example embodiments.

FIG. 2 illustrates an example of a medical device that may be utilized, in accordance with at least one or more example embodiments. In FIG. 2, a medical device may be a wearable medical device (WMD), which may be configured to facilitate monitoring and treatment of a person's heart such as, but not limited to, a wearable cardioverter defibrillator (WCD) 200. The WCD 200 may be included in a support structure 202, which may be configured to be worn by a person 204. The WCD 200 may include various electronic components to facilitate the functionality of the WCD 200 as a heart monitoring and defibrillator device. The various electronic components may be illustrated as a WCD module (hereon a WCD monitor 206). The WCD 200 may include two therapy electrodes configured to defibrillate a person's heart 208, defibrillator electrodes 210, and a number of monitoring electrodes 212 configured to detect and measure the person's electrical heart activity (e.g., electrocardiogram or ECG). As shown, the monitoring electrodes 212 and the defibrillator electrodes 210 may be located proximate to the person's heart 208 and chest area 216. The monitoring electrodes 212 and the defibrillator electrodes 210 may be communicatively coupled to the WCD monitor 206 via a number of electrical leads 214. Additionally, shown in FIG. 2, the WCD monitor 206 may include an information management module (IMM 218).

In FIG. 2, the support structure 202 may be in the form of a garment configured to be worn by the person 204. In some examples, the monitoring electrodes 212 and the defibrillator electrodes 210, shown in FIG. 2, may be configured to be wirelessly coupled with the WCD monitor 206.

As described herein, the IMM 218 included in the WCD monitor 206 may be configured to receive an indication of proximity of a healthcare device from a proximity sensor, where the indication may include healthcare device identification information and distance information of the healthcare device from the WMD 200. The IMM 218 may be configured to determine a type of healthcare device based upon the received healthcare device identification information. Once determined the type of healthcare device, the IMM 218 may be configured to communicate information regarding the WMD 200, where the communicated information may be adapted to correspond to the determined type of healthcare device in accordance with various embodiments.

In FIG. 2, the support structure 202 may be configured to support various components such as, but not limited to, the communication medium 104, the proximity sensor 106, the storage medium 108, the processor 102, and combination thereof (shown in FIG. 1). The components may be configured to facilitate the operation of the herein described functionality and disclosure.

In FIG. 2, the person 204 may experience a heart related event (e.g., an arrhythmia of some kind). The received ECG signals from the one or more electrodes 212 may indicate the onset of the heart related event, and in response, the WCD 200 may provide a therapy signal (e.g., electric shock) to treat the heart via the therapy electrodes 210 to the heart 208. In this example scenario, a layperson (not shown) may have witnessed the person 204 suffering the heart related event. The layperson may obtain a publicly available automated external defibrillator (AED) such as, but not limited to, a healthcare device 114 (shown in FIG. 1) and go over to the person 204. The IMM 218 may receive an indication that the AED is nearby via the proximity sensor 106 (shown in FIG. 1). The indication may include healthcare identification information about the AED such as, but not limited to, information that the AED may be the publicly available kind (i.e., may not be an AED commonly used by emergency and/or medical personnel, but instead, an AED that may be used by a layperson). Additionally, the IMM 218 may determine how far the AED may be located from the person 204 (i.e., WCD). Because the IMM 218 may have determined that the AED is the kind commonly used by a layperson, the IMM 218 may communicate information regarding the WCD adapted to correspond to the type of AED. In this scenario, the IMM 218 may communicate information via audio by generating an audio message such as, but not limited to, "do not remove the WCD", "do not shock patient with your AED", "dial 911", and so forth. The audio message may include some audio instructions that may be applicable to the layperson such as, but not limited to, "is the person breathing", "please start chest compressions", "is the person unconscious", etc. The audio instructions may be conveyed via a speaker included in the support structure 202 of the wearable device system 200. As a result, the communicated information may be adapted to the type of healthcare device (i.e., layperson healthcare device). Additionally, references may be made to FIG. 2 to facilitate various functionalities and configurations in accordance with various embodiments disclosed herein.

It should be appreciated after review of this disclosure that it is contemplated within the scope and spirit of the present disclosure that the claimed subject matter may include a wide variety of medical devices and healthcare devices. As described above, the WCD 200 is only but one example of a medical device. Accordingly, the claimed subject matter is not limited in these respects.

Figure 3:
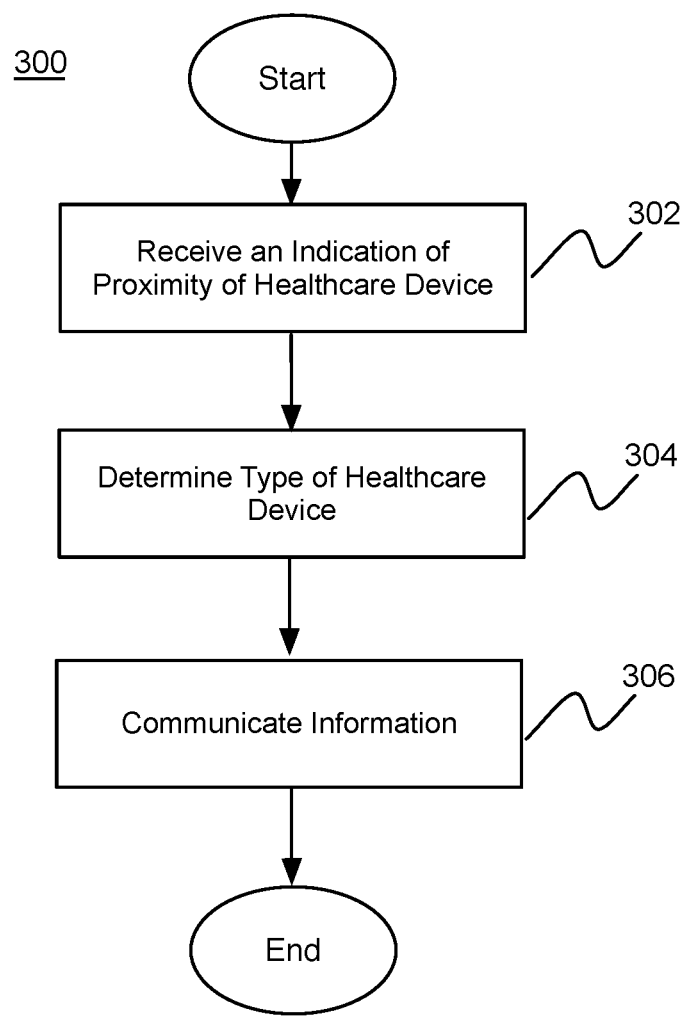
FIG. 3 illustrates an operational flow for managing communication of information regarding a medical device in accordance with various embodiments as described herein.

FIG. 3 illustrates an operational flow for managing communication of information regarding a medical device in accordance with various embodiments as described herein. In some portions of the description, illustrative implementations of the method are described with reference to the elements depicted in FIGS. 1 and 2. However, the described embodiments are not limited to these depictions.

Additionally, FIG. 3 employs block diagrams to illustrate the example methods detailed therein. These block diagrams may set out various functional block or actions that may be described as processing steps, functional operations, events and/or acts, etc., and may be performed by hardware, software, and/or firmware. Numerous alternatives to the functional blocks detailed may be practiced in various implementations. For example, intervening actions not shown in the figures and/or additional actions not shown in the figures may be employed and/or some of the actions shown in one figure may be operated using techniques discussed with respect to another figure. Additionally, in some examples, the actions shown in these figures may be operated using parallel processing techniques. The above described, and other not described, rearrangements, substitutions, changes, modifications, etc., may be made without departing from the scope of the claimed subject matter.

In some examples, operational flow 300 may be employed as part of medical device having electrical signal monitoring capabilities. Beginning at block 302 ("Receive an Indication of Proximity of Healthcare Device"), a wearable device system including a WMD, a proximity sensor, and an IMM, where the IMM may be configured to receive an indication of proximity of a healthcare device from the proximity sensor. The indication may include healthcare device identification information and distance information of the healthcare device from the WMD.

Continuing from block 302 to block 304 ("Determine Type of Healthcare Device"), the IMM may be configured to determine a type of healthcare device based upon the received healthcare device identification information. As described herein, the type of healthcare device may include a wide variety of devices and form factors such as, but not limited to, a emergency medical device, acoustic determination of a location of the IMM, a tags, etc. in accordance with various embodiments.

Continuing from block 304 to block 306 ("Communicate Information"), the IMM may be configured to communicate information regarding the WMD, the communicated information adapted to correspond to the determined type of healthcare device. The communicated information may be configured to be of use to a variety of recipients and/or devices in accordance with various embodiments.

In general, the operational flow described with respect to FIG. 3 and elsewhere herein may be implemented as a computer program product, executable on any suitable computing system, or the like. For example, a computer program product for managing communication of information regarding a medical device may be provided. Example computer program products may be described with respect to FIG. 4 and elsewhere herein.

FIG. 4 illustrates an example computer program product 400, arranged in accordance with at least some embodiments described herein. Computer program product 400 may include machine readable non-transitory medium having stored therein instructions that, when executed, cause the machine to learn whether to activate an alarm, according to the processes and methods discussed herein. Computer program product 400 may include a signal bearing medium 402. Signal bearing medium 402 may include one or more machine-readable instructions 404 which, when executed by one or more processors, may operatively enable a computing device to provide the functionality described herein. In various examples, the devices discussed herein may use some or all of the machine-readable instructions.

In some examples, the machine readable instructions 404 may include an information management module (IMM) configured to receive an indication of proximity of a healthcare device from a proximity sensor, where the indication may include healthcare device identification information and distance information of the healthcare device from a WMD. In some examples, the machine readable medium 404 may facilitate the IMM to determine a type of healthcare device based upon the received healthcare device identification information. In some examples, the machine readable medium 404 may facilitate the IMM to communicate information regarding the WMD, where the communicated information adapted to correspond to the determined type of healthcare device.

In some implementations, signal bearing medium 402 may encompass a computer-readable medium 406, such as, but not limited to, a hard disk drive, a Compact Disc (CD), a Digital Versatile Disk (DVD), a Universal Serial Bus (USB) drive, a digital tape, memory, etc. In some implementations, the signal bearing medium 402 may encompass a recordable medium 408, such as, but not limited to, memory, read/write (R/W) CDs, R/W DVDs, etc. In some implementations, the signal bearing medium 402 may encompass a communications medium 410, such as, but not limited to, a digital and/or an analog communication medium (e.g., a fiber optic cable, a waveguide, a wired communication link, a wireless communication link, etc.). In some examples, the signal bearing medium 402 may encompass a machine readable non-transitory medium.

In general, the methods described with respect to FIG. 3 and elsewhere herein may be implemented in any suitable computing system. Example systems may be described with respect to FIG. 5 and elsewhere herein. In general, the system may be configured to facilitate a smart information managing module (IMM) in accordance with various embodiments.

FIG. 5 is a block diagram illustrating an example computing device 500, such as might be embodied by a person skilled in the art, which is arranged in accordance with at least some embodiments of the present disclosure. In one example configuration, computing device 500 may include one or more processors 510 and system memory 520. A memory bus 530 may be used for communicating between the processor 510 and the system memory 520.

Depending on the desired configuration, processor 510 may be of any type including but not limited to a microprocessor (µP), a microcontroller (µC), a digital signal processor (DSP), or any combination thereof. Processor 510 may include one or more levels of caching, such as a level one cache 511 and a level two cache 512, a processor core 513, and registers 514. The processor core 513 may include an arithmetic logic unit (ALU), a floating point unit (FPU), a digital signal processing core (DSP Core), or any combination thereof. A memory controller 515 may also be used with the processor 510, or in some implementations the memory controller 515 may be an internal part of the processor 510.

Depending on the desired configuration, the system memory 520 may be of any type including but not limited to volatile memory (such as RAM), non-volatile memory (such as ROM, flash memory, etc.) or any combination thereof. System memory 520 may include an operating system 521, one or more applications 522, and program data 524. Application 522 may include information management algorithm 523 that is arranged to perform the functions as described herein including the functional blocks and/or actions described. Program Data 524 may include, among other information described, types of healthcare device data 525 for use with the information management algorithm 523. In some example embodiments, application 522 may be arranged to operate with program data 524 on an operating system 521 such that implementations of information management module (IMM) having determination and communication capabilities may be provided as described herein. For example, apparatus described in the present disclosure may comprise all or a portion of computing device 500 and be capable of performing all or a portion of application 522 such that determining the types of healthcare devices and communicating information regarding a WMD, where the communicated information adapted to correspond to the determined type of healthcare device as described herein. This described basic configuration is illustrated in FIG. 5 by those components within dashed line 501.

Computing device 500 may have additional features or functionality, and additional interfaces to facilitate communications between the basic configuration 501 and any required devices and interfaces. For example, a bus/interface controller 540 may be used to facilitate communications between the basic configuration 501 and one or more data storage devices 550 via a storage interface bus 541. The data storage devices 550 may be removable storage devices 551, non-removable storage devices 552, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 520, removable storage 551 and non-removable storage 552 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 500. Any such computer storage media may be part of device 500.

Computing device 500 may also include an interface bus 542 for facilitating communication from various interface devices (e.g., output interfaces, peripheral interfaces, and communication interfaces) to the basic configuration 501 via the bus/interface controller 540. Example output interfaces 560 may include a graphics processing unit 561 and an audio processing unit 562, which may be configured to communicate to various external devices such as a display or speakers via one or more A/V ports 563. Example peripheral interfaces 560 may include a serial interface controller 571 or a parallel interface controller 572, which may be configured to communicate with external devices such as input devices (e.g., keyboard, mouse, pen, voice input device, touch input device, etc.) or other peripheral devices (e.g., printer, scanner, etc.) via one or more I/O ports 573. An example communication interface 580 includes a network controller 581, which may be arranged to facilitate communications with one or more other computing devices 590 over a network communication via one or more communication ports 582. A communication connection is one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), infrared (IR) and other wireless media. The term computer readable media as used herein may include both storage media and communication media.

Computing device 500 may be implemented as a portion of a small-form factor portable (or mobile) electronic device such as a cell phone, a personal data assistant (PDA), a personal media player device, a wireless web-watch device, a personal headset device, an application specific device, or a hybrid device that includes any of the above functions. Computing device 500 may also be implemented as a personal computer including both laptop computer and non-laptop computer configurations. In addition, computing device 500 may be implemented as part of a wireless base station or other wireless system or device.

FIG. 6 is a block diagram illustrating components of a medical device (e.g., External Defibrillator 600), which may be used with various embodiments. These components may be, for example, a medical device 110 (shown in FIG. 1) and wearable medical device 200 (shown in FIG. 2). For simplicity, the medical device may be an example of defibrillator device.

The defibrillator device 600 may be intended for use by a user 680 (e.g., the person 204 shown in FIG. 2). The defibrillator device 600 may typically include a defibrillation port 610, such as a socket in housing 601. The defibrillation port 610 may include nodes 614 and 618. One or more electrodes 604 and 608 may be plugged in to the defibrillation port 610, so as to make electrical contact with nodes 614 and 618, respectively. It may also be possible that the electrodes 604 and 608 may be connected continuously to the defibrillation port 610, etc. Either way, the defibrillation port 610 may be used for guiding via the electrodes 604 and 608 to the person 680 an electrical charge that may have been stored in the defibrillator device 600, as described herein.

If the defibrillator device 600 comprise of a heart monitoring component, as was described herein, the defibrillator device 600 may also have an ECG port 619 in the housing 601, for receiving ECG leads 609. The ECG leads 609 may facilitate sensing of an ECG signal (e.g., a 12-lead signal or from a different number of lead signals), and electrode attachment integrity may be determined from the ECG signal, in accordance with the various embodiments disclosed herein. Moreover, a heart monitoring component could have additional ports (not shown), and the other component 625 may be configured to utilize the electrical signal (e.g., ECG signal, impedance, etc. to facilitate determination of electrode leads off from the skin of the user 680), in accordance with various embodiments.

The defibrillator 600 also may include a measurement circuit 620. The measurement circuit 620 may receive physiological signals from the ECG port 619, and also from other ports, if provided (e.g., previously described lead-off circuitry). The circuit 620 may render detected physiological signals and their corresponding information. The information may be in the form of data, or other signals, etc.

The measurement circuit 620 may obtain physiological signals through the nodes 614 and 618 instead, when the electrodes 604 and 608 are attached to the person 680 (i.e., the skin). In these cases, a person's ECG signal may be detected as a voltage difference between the electrodes 604 and 608. Additionally, the impedance between the electrodes 604 and 608 may detect, among other things, whether the electrodes 604 and 608 have been inadvertently disconnected from the skin of the person 680.

The defibrillator 600 may also include a processor 630. The processor 630 may be implemented in a wide variety of manners for causing actions and operations to be performed. Some examples may include digital and/or analog processors such as microprocessors and digital-signal processors (DSPs), controllers such as microcontrollers, software running in a machine environment, programmable circuits such as Field Programmable Gate Arrays (FPGAs), Field-Programmable Analog Arrays (FPAAs), Programmable Logic Devices (PLDs), Application Specific Integrated Circuits (ASICs), and so on or any combination thereof.

The processor 630 may include a number of modules. One example module may be a signal processing module 632, which may detect outputs from the measurement circuit 620. The signal processing module 632 may include electronic components configured to determine types of healthcare devices and communicate information regarding a WMD, where the communicated information may be adapted to correspond to the determined type of healthcare device such as, but not limited to the various processes described above. Accordingly, the communicated information may be adapted to the type of healthcare device (i.e., layperson healthcare device, medical professional device, emergency personnel device, etc).

In another example, advice module 634 may provide advice based, at least in part, on outputs of signal processing module 632. The advice module 634 may include an algorithm such as, but not limited to, Shock Advisory Algorithm, implement decision rules, and so on. For example, the advice may be to shock, to not shock, to administer other forms of therapy, provide an indication to confirm a health status of the person 680 (e.g., determine whether the person 680 is experiencing perfusing or non-perfusing ventricular tachycardia (VT), and so on. If the advice is to shock, some defibrillator examples may report the advice to the user and prompt them to do it. In other examples, the defibrillator device may execute the advice by administering the shock. If the advice is to administer CPR, the defibrillator 600 may further issue prompts for administrating CPR, and so forth. Examples of Shock Advisory Algorithm may be found in US patent application U.S. Ser. No. 15/421,165, filed Jan. 31, 2017 (now issued as U.S. Pat. No. 10,016,614) titled Wearable cardioverter defibrillator (WCD) system making shock/no shock determinations by aggregating aspects of multiple patient parameters, which is incorporated by reference in its entirety for all purposes.

The processor 630 may include additional modules, such as module 636 for various other functions such as, but not limited to, information management module (IMM) 836, as described herein.

In an example, the defibrillator device 600 may include a memory 638, which may work together with the processor 630. The memory 638 may be implemented in a wide variety of manners. For example, the memory 638 may be implemented such as, but not limited to, nonvolatile memories (NVM), read-only memories (ROM), random access memories (RAM), and so forth or any combination thereof. The memory 638 may include programs for the processor 630, and so on. For example, the memory 638 may include ECG signals for determining a respiration rate post-event. The programs may include operational programs executed by the processor 630 and may also include protocols and methodologies so that decisions may be made by advice module 634. Additionally, the memory 638 may store various prompts for the user 680, etc. Moreover, the memory 638 may store a wide variety of information (i.e., predetermined parameter data) such as, but not limited to information regarding the person 680.

The defibrillator 600 may also include a power source 640. In order to facilitate portability of defibrillator device 600, the power source 640 may include a battery type device. A battery type device may be implemented as a battery pack, which may be rechargeable or not-rechargeable. At times, a combination of rechargeable and non-rechargeable battery packs may be utilized. Examples of power source 640 may include AC power override, where AC power may be available, and so on. In some examples, the processor 630 may control the power source 640.

Additionally, the defibrillator device 600 may include an energy storage module 650. The energy storage module 650 may be configured to store some electrical energy (e.g., when preparing for sudden discharge to administer a shock). The energy storage module 650 may be charged from the power source 640 to an appropriate level of energy, as may be controlled by the processor 630. In some implementations, the energy storage module 650 may include one or more capacitors 652, and the like.

The defibrillator 600 may include a discharge circuit 655. The discharge circuit 655 may be controlled to facilitate discharging of the energy stored in energy storage module 650 to the nodes 614 and 618. The discharge circuit 655 may include one or more switches 657. The one or more switches 657 may be configured in a number of manners such as, but not limited to, an H-bridge, and so forth.

The defibrillator device 600 may further include a user interface 670 for the user 680. The user interface 670 may be implemented in a variety of manners. For example, the user interface 670 may include a display screen capable of displaying what is detected and measured, provide visual feedback to the user 680 for their resuscitation attempts, and so forth. The user interface 670 may also include an audio output such as, but not limited to, a speaker to issue audio prompts, etc. The user interface 670 may additionally include various control devices such as, but not limited to, pushbuttons, keyboards, switches, track pads, and so forth. Additionally, the discharge circuit 655 may be controlled by the processor 630 or directly by the user 680 via the user interface 670, and so forth.

Additionally, the defibrillator device 600 may include other components. For example, a communication module 690 may be provided for transmitting ECG signals stored on the defibrillator device 600 to be downloaded and processed as described above. Such communication may be performed wirelessly, or via wire, or by infrared communication, near field communication (NFC), Bluetooth, WiFi, and so forth. Accordingly, information may be communicated, such as person data, incident information, therapy attempted, CPR performance, ECG information, and so forth.

A feature of a defibrillator device may be CPR related prompting. CPR prompts may be issued to the user 680 visually or by audio facilitating assistance in the administration of CPR by the user 680. Examples may be found in U.S. Pat. Nos. 6,334,070 and 6,356,785.

It should be appreciated after review of this disclosure that it is contemplated within the scope and spirit of the present disclosure that the claimed subject matter may include a wide variety of healthcare devices. Accordingly, the claimed subject matter is not limited in these respects.

Some portions of the foregoing detailed description are presented in terms of algorithms or symbolic representations of operations on data bits or binary digital signals stored within a computing system memory, such as a computer memory. These algorithmic descriptions or representations are examples of techniques used by those of ordinary skill in the data processing arts to convey the substance of their work to others skilled in the art. An algorithm is here, and generally, considered to be a self-consistent sequence of operations or similar processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has proven convenient at times, principally for reasons of common usage, to refer to such signals as bits, data, values, elements, symbols, characters, terms, numbers, numerals or the like. It should be understood, however, that all of these and similar terms are to be associated with appropriate physical quantities and are merely convenient labels. Unless specifically stated otherwise, as apparent from the following discussion, it is appreciated that throughout this specification discussion utilizing terms such as "processing," "computing," "calculating," "determining" or the like refer to actions or processes of a computing device that manipulates or transforms data represented as physical electronic or magnetic quantities within memories, registers, or other information storage devices, transmission devices, or display devices of the computing device.

Claimed subject matter is not limited in scope to the particular implementations described herein. For example, some implementations may be in hardware, such as those employed to operate on a device or combination of devices, for example, whereas other implementations may be in software and/or firmware. Likewise, although claimed subject matter is not limited in scope in this respect, some implementations may include one or more articles, such as a signal bearing medium, a storage medium and/or storage media. This storage media, such as CD-ROMs, computer disks, flash memory, or the like, for example, may have instructions stored thereon that, when executed by a computing device such as a computing system, computing platform, or other system, for example, may result in execution of a processor in accordance with claimed subject matter, such as one of the implementations previously described, for example. As one possibility, a computing device may include one or more processing units or processors, one or more input/output devices, such as a display, a keyboard and/or a mouse, and one or more memories, such as static random access memory, dynamic random access memory, flash memory, and/or a hard drive.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be affected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skilled in the art in light of this disclosure. In addition, those skilled in the art will appreciate that the mechanisms of the subject matter described herein are capable of being distributed as a product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a flexible disk, a hard disk drive (HDD), a Compact Disc (CD), a Digital Versatile Disk (DVD), a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity, control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Reference in the specification to "an implementation," "one implementation," "some implementations," or "other implementations" may mean that a particular feature, structure, or characteristic described in connection with one or more implementations may be included in at least some implementations, but not necessarily in all implementations. The various appearances of "an implementation," "one implementation," or "some implementations" in the preceding description are not necessarily all referring to the same implementations.

While certain exemplary techniques have been described and shown herein using various methods and systems, it should be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter is not limited to the particular examples disclosed, but that such claimed subject matter also may include all implementations falling within the scope of the appended claims, and equivalents thereof.

What is claimed:

1. A wearable device system comprising:
a wearable medical device (WMD) configured to be worn by a person;
a proximity sensor; and
an information management module (IMM), the IMM communicatively coupled to the proximity sensor, the IMM configured to:
receive an indication of proximity of a healthcare device from the proximity sensor, the indication including healthcare device identification information and distance information of the healthcare device from the WMD,
determine a type of healthcare device based upon the received healthcare device identification information, wherein the type of healthcare device comprises at least one of a layperson healthcare device and a professional healthcare device, and
communicate information regarding the WMD to a user of the healthcare device based on the determined type of the healthcare device, wherein the information to be communicated to the user varies based on the determined type of healthcare device, and wherein the communicated information is related to health of the person or treatment of the person wearing the WMD.

2. The wearable device system of claim 1, wherein the IMM is configured to communicate the information regarding the WMD to a bystander.

3. The wearable device system of claim 1, wherein the layperson healthcare device is a device for use by a layperson and the professional healthcare device is a device for use by an emergency medical technician (EMT) or a medical professional.

4. The wearable device system of claim 1, wherein to determine the type of healthcare device, the IMM is configured to determine whether the healthcare device is located in a medical facility.

5. The wearable device system of claim 1, wherein the WMD comprises a wearable cardioverter defibrillator (WCD).

6. The wearable device system of claim 1, wherein the proximity sensor comprises an infrared (IR) based proximity sensor.

7. The wearable device system of claim 1, wherein the IMM is configured to communicate the information regarding the WMD via an audio communication medium.

8. The wearable device system of claim 1, wherein the IMM is configured to communicate the information regarding the WMD via a user interface medium.

9. The wearable device system of claim 1, wherein the healthcare device corresponds to another WMD.

10. The wearable device system of claim 1, wherein the IMM is further configured to detect a tag associated with a healthcare personnel to receive the indication of proximity of the healthcare device associated with the healthcare personnel.

11. The wearable device system of claim 10, wherein the tag comprises a radio frequency identification (RFID) tag on the healthcare personnel.

12. A wearable device system comprising:
a wearable medical device (WMD) configured to be worn by a person;
a proximity sensor; and
an information management module (IMM), the IMM communicatively coupled to the proximity sensor, the IMM configured to:
receive an indication of proximity of a healthcare device from the proximity sensor, the indication including healthcare device identification information and distance information of the healthcare device from the WMD, and
provide information to a person associated with the healthcare device based on a type of the healthcare device, wherein the information is related to health of the person wearing the WMD or treatment of the person wearing the WMD.

13. The wearable device system of claim 12, wherein the type of healthcare device comprises at least one of a layperson healthcare device and a professional healthcare device, and wherein the layperson healthcare device is a device for use by a layperson and the healthcare device is a device for use by an emergency medical technician (EMT) or a medical professional.

14. The wearable device system of claim 12, wherein the information related to the health of the person wearing the WMD includes clinical information.

15. The wearable device system of claim 14, wherein the clinical information includes at least one of electrocardiogram (ECG) data, electric charge that has been administered, and time of a heart related event associated with the person wearing the WMD.

16. The wearable device system of claim 12, wherein the information related to the health of the person wearing the WMD includes information related to monitoring of the person wearing the WMD.

17. The wearable device system of claim 12, wherein the information is provided to the person associated with the healthcare device via an audio or a visual communication medium.

18. The wearable device system of claim 12, wherein the healthcare device corresponds to another WMD having an electronic tag, and wherein the electronic tag includes the healthcare device identification information.

19. The wearable device system of claim 12, wherein the information related to the treatment of the person wearing the WMD includes guidance or instructions to facilitate the treatment of the person wearing the WMD, and wherein the guidance or instructions include inquiries related to a status of the person wearing the WMD.

* * * * *